(12) United States Patent
Holland

(10) Patent No.: US 7,383,079 B2
(45) Date of Patent: Jun. 3, 2008

(54) NONLINEAR METHOD AND APPARATUS FOR ELECTROCARDIOGRAM PACEMAKER SIGNAL FILTERING

(75) Inventor: Alexander Holland, West Linn, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 266 days.

(21) Appl. No.: 11/099,849

(22) Filed: Apr. 6, 2005

(65) Prior Publication Data
US 2005/0234361 A1    Oct. 20, 2005

Related U.S. Application Data

(60) Provisional application No. 60/560,677, filed on Apr. 8, 2004.

(51) Int. Cl.
*A61B 5/0402* (2006.01)
(52) U.S. Cl. ...................................... 600/509
(58) Field of Classification Search ............ 600/508
See application file for complete search history.

(56) References Cited

U.S. PATENT DOCUMENTS

| 5,259,387 A | 11/1993 | dePinto |
| 5,448,997 A | 9/1995 | Kruse et al. |
| 5,630,425 A | 5/1997 | Panescu et al. |
| 5,660,184 A * | 8/1997 | Donehoo et al. ............ 600/509 |
| 5,817,133 A * | 10/1998 | Houben ......................... 607/9 |
| 5,825,672 A | 10/1998 | Brudnoy |
| 5,924,980 A | 7/1999 | Coetzee |
| 2003/0023176 A1 | 1/2003 | Yonce et al. |

FOREIGN PATENT DOCUMENTS

EP    0 748 637 A2    12/1996

* cited by examiner

*Primary Examiner*—Carl H. Layno
*Assistant Examiner*—Eric D Bertram
(74) *Attorney, Agent, or Firm*—Hiscock & Barclay, LLP

(57) ABSTRACT

Signal "peak" and "valley" removal properties of mathematical morphology operators are exploited in a method and apparatus for detecting, removing, or improving fidelity of pacemaker signal components of the Electrocardiogram (ECG) at sampling rates well below the pacemaker signal Nyquist rate. The method works for the wide variability in pacemaker signal amplitude, width, firing frequency, and other characteristics encountered in practice, and it works for malfunctioning pacemakers that may fire at any point relative to the QRS complex of the ECG signal. Filtering operations require minimal digital storage and are computationally inexpensive (no multiplications), mainly involving "maximum" and "minimum" type signal detections over a finite time history of the input signal. This implies that the method can be inexpensively implemented on small instruments in either hardware or software. The method may also be used to estimate the height and polarity of the pacemaker voltage spike, even though the base sampling period may be longer than the width of the spike.

24 Claims, 18 Drawing Sheets

```
#define  MAX(x, y)    (((x) > (y))? (x): (y))
define  INT_MIN      0x80000000 int
Dilate( long   *pIn,    // Pointer to input signal buffer
        int    lenIn,   // Length of input signal buffer, pIn.
        int    m;       // Index of pIn for next unprocessed input sample.
        long   *pK,     // Pointer to kernel coefficients.
        int    lenK )   // Length of kernel pK.
{
   int     j, first, remaining;
   long    out;

first     = m + 1 - len;   // First input sample.
   remaining = MAX(-first, 0); // Wrapped samples (circular buf).
   first     = MAX(first, 0);  // First input sample.

// Initialize the oldest output signal value to a small negative value.
   out = INT_MIN.

// Replace the oldest output signal value with a new value.
   for(j = first; j <= m; j++)
        out = MAX(out, *(pIn + j) + *(pK + m - j) );

// If the beginning of the input signal buffer was reached, wrap
   // to the other end to continue the computation.
   for(j = 1; j <= remaining; j++)
        out = MAX(out, *(pIn + lenIn-j) + *(pK + m + j) );

return out;
}
```

Figure 7

NONLINEAR METHOD AND APPARATUS FOR ELECTROCARDIOGRAM PACEMAKER SIGNAL FILTERING

CROSS REFERENCE TO RELATED APPLICATION

This application is based upon a provisional patent application, U.S. Ser. No. 60/560,677, filed Apr. 8, 2004, under 35 USC §119(e), the entire contents of which are herein incorporated by reference.

FIELD OF THE INVENTION

The invention relates to the field of electrocardiogram (ECG) digital signal processing, and more specifically to the application of digital filtering as used in order to improve ECG signal qualities for automated machine analysis and/or human interpretation.

BACKGROUND OF THE INVENTION

Because the ECG signal bandwidth typically observed for clinical diagnosis is less than 75 Hz, sampling rates that range between 150 and 500 Hz are sufficient to support clinical interpretation or automated machine analysis. If a pacemaker (pacer) signal is added to the ECG signal, this sampling rate is no longer adequate for the pacer signal component because a significant portion of its energy is at frequencies greater than 250 Hz. Increasing the sampling rate in order to accommodate the pacer signal component would add significant cost and expense to all devices and systems processing and storing the increased flow rate and quantity of data.

Because the pacer signal component can be a relatively tall (up to 700 mV) and narrow (~0.1-2 ms) impulse that either triggers infrequently on demand or fires approximately 60 times per minute, it also contributes significant low-frequency energy overlapping the bandwidth of the core ECG signal. This fundamentally limits the effectiveness of linear filtering techniques, even at higher sampling rates. Moreover, if the pacer is malfunctioning, it can fire asynchronous to the QRS complex, or fire synchronous to the QRS complex, but out of proper phase so that the pacer spike sits on top of the R wave, for example. Other practical challenges are that the signal can: (a) range in amplitude from a fraction of the QRS amplitude to 100 times larger, (b) have significant undershoot or overshoot (e.g., biphasic), and (c) have a relatively long (e.g., >40 ms) settling time.

Nevertheless, it is desirable to process (that is, either detect, remove, and/or estimate) an ECG signal with a pacer component without increasing the sampling rate, while minimizing pacer signal related distortion. For waveform analysis, it is desirable to remove the pacer signal component without significant distortion regardless of the amplitude, phase, and synchronicity of the pacer signal relative to the QRS complex. Otherwise, pacer signals could be misinterpreted for example, as abnormal premature ventricular contractions. Poorly removing the signal, on the other hand, could increase the probability of additional analysis error.

SUMMARY OF THE INVENTION

The pacer filtering method and mechanism described herein effectively overcomes the above-noted limitations, operates under these "real world" conditions, and provides other benefits.

According to one aspect of the present invention, there is disclosed a method to at least one of detecting, removing and estimating a pacemaker signal from an electrocardiogram ("ECG") signal of a human or animal to diagnose a physiological condition, the method comprising the steps of:
   digitizing a plurality of ECG potentials (M channels of ECG lead data) with an analog to digital converter ("ADC") to create a discrete signal representation of each potential in time;
   filtering the plurality of ECG potentials using a digital filter to create a plurality of filtered ECG potentials;
   operating on the plurality of filtered ECG potentials using a non-linear mathematical morphology function to detect and remove the pacer maker signal from the ECG signal to create a plurality of processed ECG potentials; and
   diagnosing a physiological condition of the human or animal based on the processed ECG potentials.

According to another aspect of the present invention, there is disclosed an electrocardiogram ("ECG") apparatus to at least one of detecting, removing and estimating pacemaker pacer signals from an ECG waveform to diagnose a physiological condition of a human or animal, the apparatus comprising:
   ECG electrodes to pickup a plurality of ECG potentials (M channels of ECG lead data) from the body of the human or animal being diagnosed, the electrodes electrically coupled to the body and connected to an ECG input;
   an analog to digital converter ("ADC") electrically connected to the ECG input, the ADC to digitize the ECG potentials and to create a discrete signal representation of each potential in time;
   a filter block electrically coupled to the ADC to transfer the discrete signal representation of each potential in time to the filter block, the filter block to perform digital filtering on the discrete signal representation of each potential and to create a plurality of filtered ECG potentials;
   a non-linear pacer filter electrically coupled to the filter block to receive the plurality of filtered ECG potentials, the non-linear pacer filter to perform at least one non-linear mathematical morphology function on the filtered ECG potentials to detect and remove the pacer signal from the ECG waveform and to create at least one processed ECG waveform; and
   a display to allow viewing of the processed ECG waveform to diagnose a physiological condition of a human or animal based at least in part on the viewing of the processed ECG waveform.

The method and apparatus for detecting, removing, or improving the pacer signal without significant distortion at low sampling rates described herein is based on the application of "mathematical morphology" operators. The present method operates in real-time on a sampled input ECG data stream and produces an output data stream either with the pacer signal removed or with a more accurate representation of the pacer signal.

Morphological operators are used according to the present invention in order to remove "peaks" and "valleys" in an ECG signal whose widths are less than a specified threshold, without injecting significant distortion into peaks and valleys above the specified threshold. This capability is important because a (biphasic) pacer spike is a component of the ECG signal with a significantly narrower peak, valley, or peak/valley characteristic than any other component in the ECG signal. This key discriminating characteristic allows the method to succeed regardless of where the pacer spike is located in relation to the QRS complex. The above method also succeeds regardless of the relative amplitudes of the peaks/valleys, so a large pacer spike is not a problem. In addition, no explicit signal is needed in order to flag the exact or approximate location of the pacer spike, as is required by other methods.

One or more "kernel functions" fine-tune the discriminating characteristics of the filter appropriately for a particular environment (sampling rate, etc.). A kernel function is non-zero for a finite interval of samples and zero otherwise (analogous to the impulse response of a finite impulse response digital filter or a finite "window" used for smoothing in spectral estimation). Generally, shorter kernels cause the removal of narrower peaks and valleys, while leaving wider ones alone.

Although the morphological operators will not cause significant distortion to other components of the QRS complex, they can cause minor rounding of the tips of the wider peaks and valleys of the QRS complex. In order to avoid this noted effect, a further aspect of the herein described method and apparatus is the ability to switch dynamically in real-time between a linear input-to-output delay operator and the above-noted morphological operators. The switch is free of transient response effects, extra delays, distortion, and/or loss of data. Given a separate external signal to flag the presence of a pacer signal spike, or by using the morphological operators to automatically detect the spike, the morphological operators generate the output samples in the proximity of the pacer spike. Outside of this proximity, the linear operator generates the output samples distortion-free. The input-output delay of the linear filter should preferably be set to match the input-output delay of the morphological operators.

It may sometimes be beneficial to always filter using the morphological operators (and not switch dynamically to the linear delay operator). For example, these operators provide an added benefit of removing impulsive noise sources (narrow noise spikes corrupting the ECG signal) that may be present in some environments.

In the case where the sampling rate is below the pacer bandwidth Nyquist rate, or when the sampling period is comparable to or longer than the firing width of the pacer signal (e.g. the entire pacer fire event could be missed because it occurred between samples), the method can statistically estimate (learn) the characteristics of the pacer spike with increasing accuracy over time, provided a marker signal indicates the sample corresponding to the pacer spike. The method's detection process can provide this marker, or an external marker signal or combination of external/internal marker can be used. Some ECG monitoring instruments employ special circuitry to detect the pacer spike and provide this marker. Because the firing of the pacer is not synchronous to the sampling period, samples represent different points along the pacer spike and hence can be used to estimate the polarity and height of the spike.

BRIEF DESCRIPTION OF THE DRAWINGS

FIG. 7 is an exemplary software implementation of the single-channel Dilate Filter;

DETAILED DESCRIPTION

Figure 1:
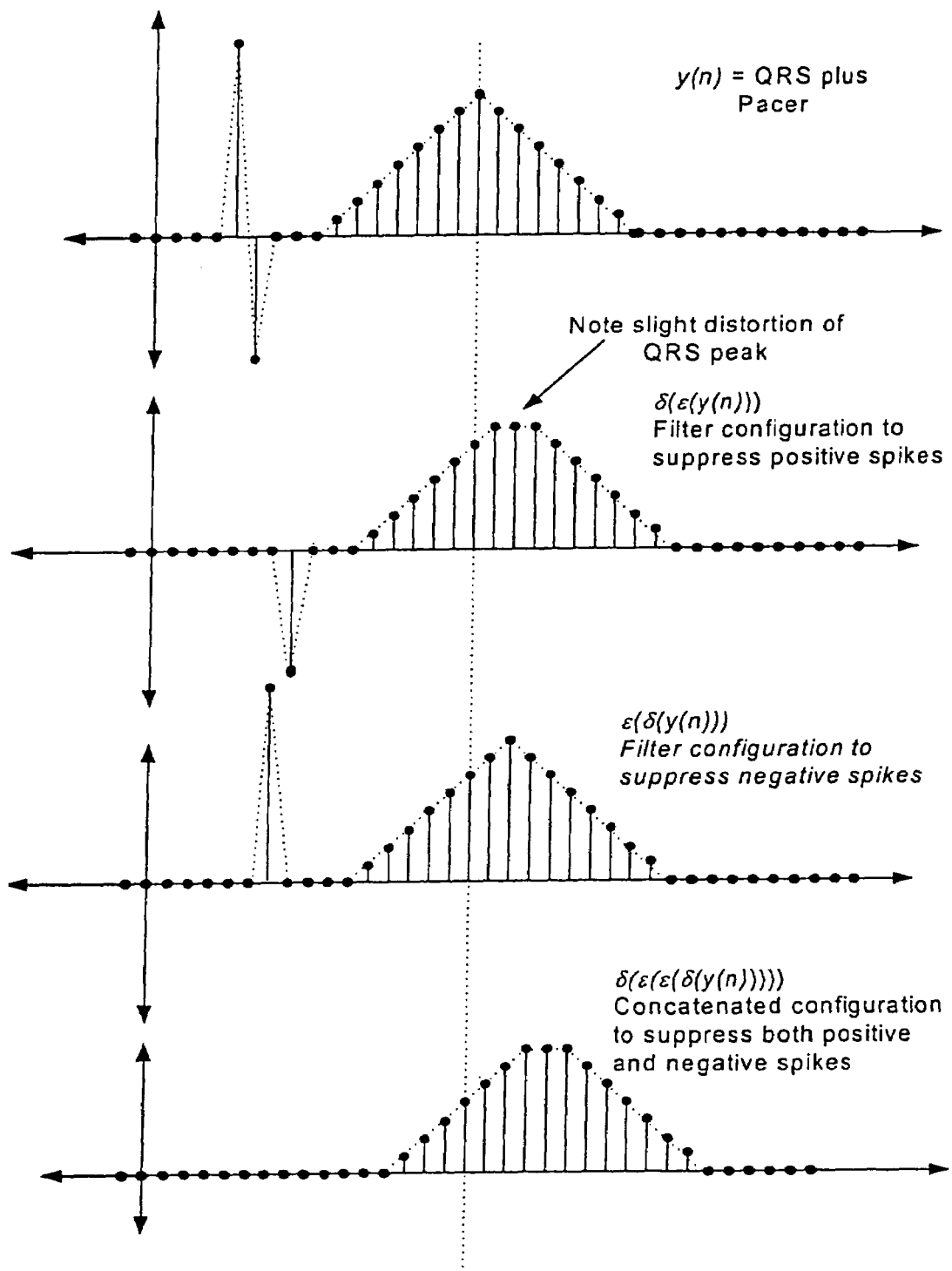
FIG. 1 is an example of the filtering properties of mathematical morphology operators.

It is commonly known that characteristics of a typical ECG signal include a periodic repetition of sequential pulses or "waves" labeled "P", "Q", "R", "S" and "T" each associated with stages of the heart's periodic electrical depolarization and re-polarization that controls its pumping action. The Q, R, and S pulses are contiguous and form the "QRS complex", in which the R wave is dominant. The Q and S pulses are often indistinguishable from the noise floor.

In ECG signals over the range of patients covering neonatal to adult, these pulses have the following typical duration and amplitude characteristics.

| Pulse Name | Duration (ms) | Amplitude (mV) |
| --- | --- | --- |
| P | 20 to 100 | ±0.0 to ±0.3 |
| QRS | 20 to 120 | ±0.5 to ±5.0 |
| T | 20 to 120 | ±0.2 to ±1.2 |

The preceding pulse dimensions are in sharp contrast with that of a typical pacemaker signal pulse that ranges in amplitude from approximately ±2 mV to ±700 mV and in duration from about 0.1 ms to 2 ms. Because the pacer signal spike is so much shorter in duration than the preceding pulses, its bandwidth is much greater than the bandwidth of each of the P, QRS, or T pulses.

The presently described method and apparatus exploits the capability of mathematical morphology functions in order to remove "peaks" and "valleys" in a signal having widths that are smaller than a specified threshold, while leaving wider peaks and valleys alone. This is particularly useful because the narrow width of the pacer spike relative to other pulses in the QRS complex is a key distinguishing property, regardless of where the pacer signal spike occurs in relation to the QRS complex. A normal functioning pacer signal is the externally generated cause of (QRS pulses, which should typically occur within about 40 ms after the occurrence of the pacer spike. However, the pulse of a malfunctioning pacer could appear synchronously at any phase relative to the QRS complex, or fire asynchronously to appear randomly along any point of the ECG signal.

Consider the "Dilate" and "Erode" mathematical morphology functions, $$\text{Dilate: } \delta_k(y(n)) = \max_{0 \le m < N} \{y(n-m) + k(m)\}$$

$$\text{Erode: } \varepsilon_k(y(n)) = \min_{0 \le m < N} \{y(n-m) - k(m)\}$$

in which the kernel function for each morphological operator is given by the vector function, $$k(n) = \begin{bmatrix} k_0(n) \\ k_2(n) \\ \dots \\ k_{M-1}(n) \end{bmatrix} \in R^M$$

This function is non-zero for n=0, 1, 2, 3, ..., N−1 and equal to 0 otherwise. The max( ) and min( ) functions apply to each element of the vector individually. Kernel coefficients are added to (subtracted from) a delayed, time-reversed y(n) and the output is equal to the maximum (minimum) over the interval where kernel coefficients are non-zero. This is analogous to convolution—equate "kernel coefficient add" to "coefficient multiplication" and the max( ) operation to accumulation.

To illustrate the signal peak and valley removal properties of the above morphology functions, consider the particular kernel function, $$k(n) = \begin{cases} c & \text{for } n = 0, 1, \dots, N-1 \\ 0 & \text{otherwise} \end{cases}$$

Because this kernel function has a constant value c over a finite interval, the Dilate and Erode operators reduce to the following equivalent (and less computationally expensive) functions:

$$\text{Dilate: } \delta_0(y(n)) = \max_{0 \le m < N} \{y(n-m)\}$$

$$\text{Erode: } \varepsilon_0(y(n)) = \min_{0 \le m < N} \{y(n-m)\}$$

In this case, the concatenated function, $\delta_0(\varepsilon_0(y(n)))$ will remove all signal peaks less than N samples in duration, and $\varepsilon_0(\delta_0(y(n)))$ will remove all signal valleys less than N samples in duration. The concatenation $\delta_0(\varepsilon_0(\varepsilon_0(\delta_0(y(n)))))$ removes both peaks and valleys. FIG. 1 shows these functions (N=3) applied to a simulated ECG signal sampled at 181 Hz with a 2-sample biphasic pacer signal spike preceding the QRS complex.

Figure 2:
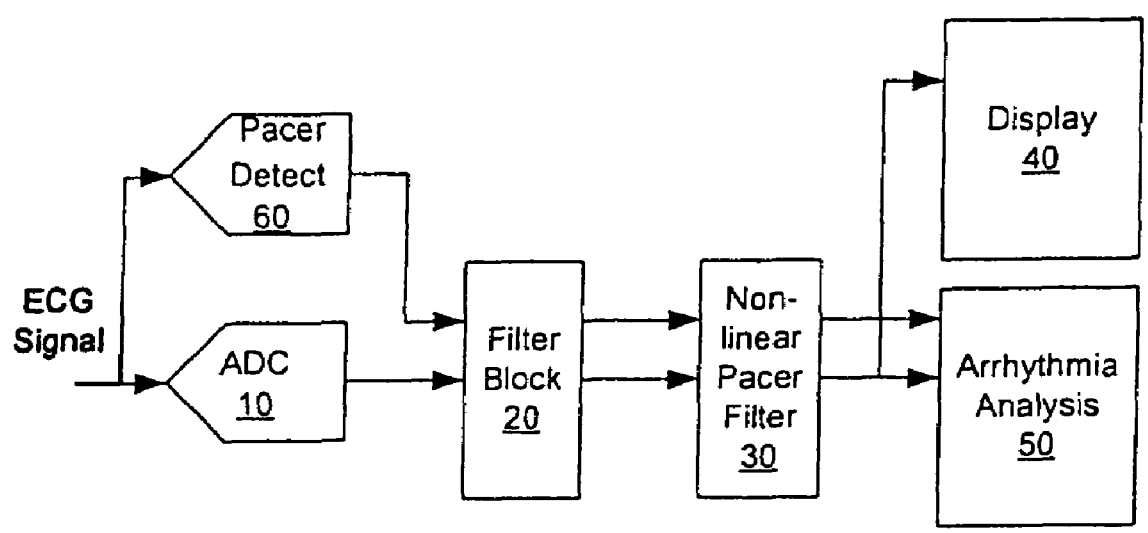
FIG. 2 is a diagram of a system incorporating a preferred embodiment of the present invention.

FIG. 2 illustrates one particular system for collecting, filtering, displaying, and analyzing ECG signal data that incorporates the present invention. An analog to digital converter (ADC) 10 translates the analog ECG input signal into a stream of digital values representing the amplitude of the analog signal at equally spaced time intervals known as the sample or sampling period. The reciprocal of the sample period is the sampling frequency, which typically is greater than 150 Hz. Data from the ADC 10 flows to filter block 20 that typically consists of processing to remove noise, such as AC power-line interference or low-frequency signal drift ("baseline wander" occurring due to body movement, breathing etc.,). From filter block 20, the data flows to a non-linear pacer filter 30, described herein. The output of pacer filter 30 feeds into both a display 40 and an arrhythmia analysis unit 50. Display 40 consists of software, circuitry and components, such as a Liquid Crystal Display (LCD), used to graphically chart the ECG signal. Arrhythmia analysis unit 50 is a sophisticated pattern recognition subsystem (implemented using software and optionally additional computing hardware) to automatically analyze the ECG signal for characteristics such as heart rate, and pathological events such as ventricular fibrillation. Optionally, the system includes a hardware pacer detect 60 that generates a pacer marker or flag indicative of which samples from the ADC 10 contain pacer signal energy. The flag remains synchronized with the digitized data from the ADC 10 as the data flows through the remainder of the system.

Figure 3:
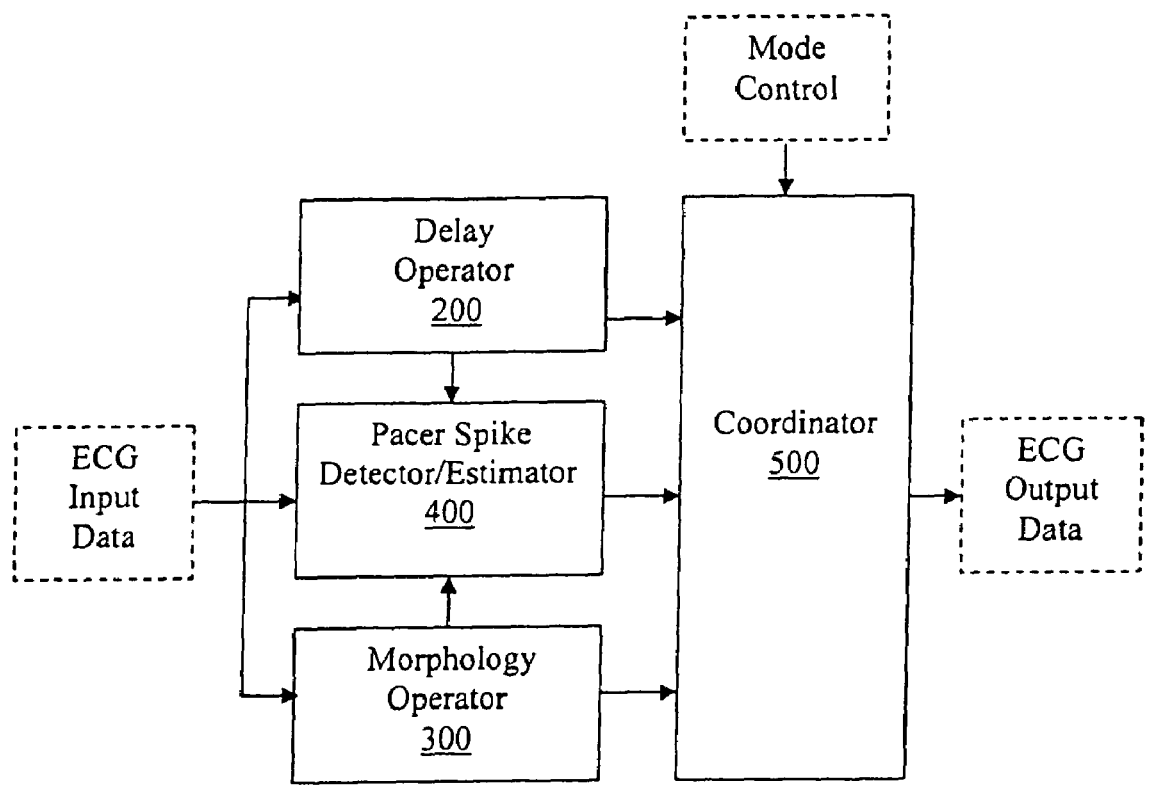
FIG. 3 is a general block diagram of the apparatus in accordance with a preferred embodiment of the present invention.

FIG. 3 depicts a general block diagram of non-linear pacer filter 30 in accordance with a preferred aspect of the invention that can be implemented using hardware, software, or a combination of the two. ECG Input Data is defined by M channels of ECG lead data from normal or paced individuals represented by vector $$y(n) = \begin{bmatrix} y_0(n) \\ y_1(n) \\ \dots \\ y_{M-1}(n) \end{bmatrix} \in R^M, \quad (5)$$

and Q channels of flags signals represented by vector $$f(n) = \begin{bmatrix} f_0(n) \\ f_1(n) \\ \dots \\ f_{Q-1}(n) \end{bmatrix} \in R^Q \quad (6)$$

Each ECG channel, $y_i(n)$, provides an input sequence of uniformly sampled k-bit (integer or floating point) data words that are to be processed. Each flags channel, $f_i(n)$, provides qualitative information about the data samples, such as the presence of a pacer spike or data corruption due to any number of practical causes, such as loss of communications. For efficiency, the flags signal could alternatively be a single channel of binary signals in which each bit of the signal represents the presence or absence of a property. The same ECG Input Data is fed into a Delay Operator 200, the Morphology Operator 300, and the Pacer Spike Estimator 400. These subsystems 200, 300, 400 provide input to a Coordinator 500 that forms the final processed output, in the form:

$$\hat{y}(n) = \begin{bmatrix} \hat{y}_0(n) \\ \hat{y}_1(n) \\ \ldots \\ \hat{y}_{M-1}(n) \end{bmatrix} \in R^M, \quad \hat{f}(n) = \begin{bmatrix} \hat{f}_0(n) \\ \hat{f}_1(n) \\ \ldots \\ \hat{f}_{Q-1}(n) \end{bmatrix} \in R^Q$$

Figure 4:
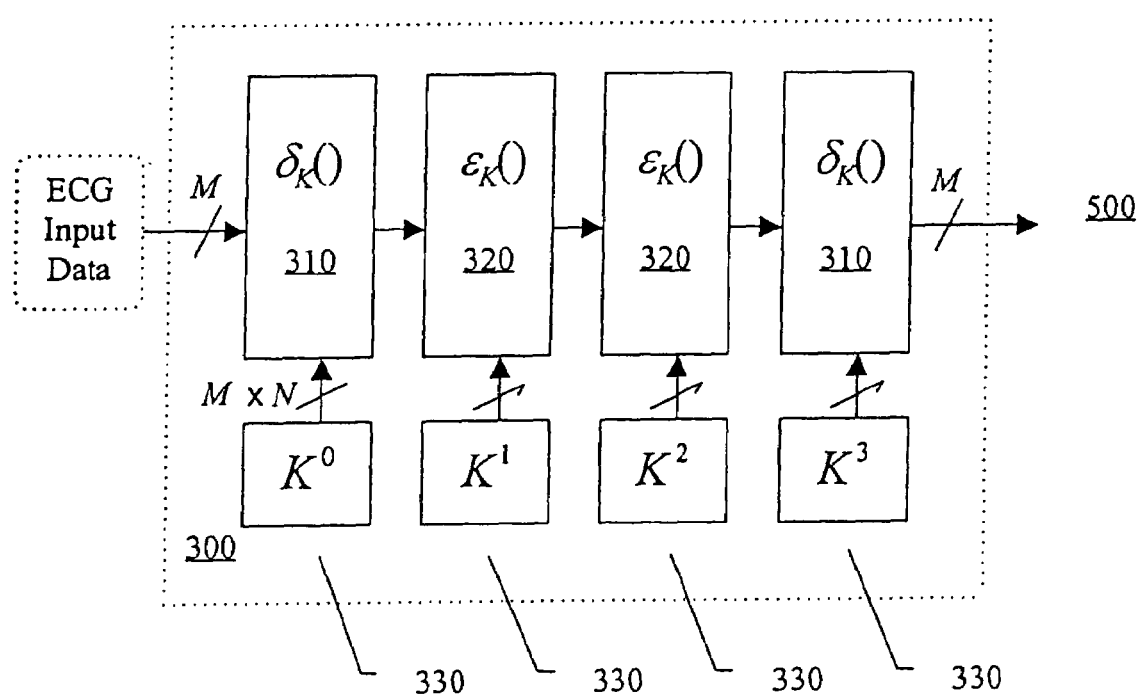
FIG. 4 is an expanded block diagram of the Mathematical Morphology Filter Unit of FIG. 3.

According to the invention, the Morphology Operator 300 provides the pacer signal removal function of the present apparatus. FIG. 4 illustrates an implementation diagram in accordance to one embodiment. The two 310 units each implement a "Dilate" morphological operation (see the defining equation above), while the two 320 units each implement an "Erode" morphological operation (see the defining equation above). This particular implementation is structured and tuned (via kernel selection) for a signal valley removal (a unit 310 followed by a unit 320) concatenated with a signal peak removal (a unit 320 followed by a unit 310). Note that the order of these two operations could alternatively be reversed. Additional stages could also be added, for example, to tune the implementation for additional filtering functions.

Units 330 in FIG. 4 are digital memory used to implement the above kernel function using a matrix of coefficients, as follows:

$$K = \begin{bmatrix} k_{0,0} & k_{0,1} & \cdots & k_{0,N-1} \\ k_{1,0} & k_{1,1} & 0 & \vdots \\ \vdots & 0 & \ddots & 0 \\ k_{M-1,0} & \cdots & 0 & k_{M-1,N-1} \end{bmatrix}$$

Each kernel matrix K is given a superscript to emphasize that its coefficients need not be the same as the kernel coefficients of other operators. However, kernel coefficients may be exactly the same for two or more of the operators, in which case these operators may share the same kernel matrix. Kernel coefficients for different operators may also have simple algebraic or symmetry relationships (e.g. reversed order, negative, etc.) that allow the operators to share the same kernel matrix by applying simple mappings, e.g. the elements of $K^1$ could be the time reverse of the elements of $K^0$, $$k_{i,j}^1 = k_{N-i,j}^0.$$

Symmetry or other mappings can also reduce kernel storage for a single morphology operator. Only the unique coefficients need be stored. For example, if the coefficients for each channel are the same, only one row of this matrix need be stored in memory. Or if the kernel is symmetrical in time, only half the coefficients need be stored. If the coefficients for each channel are constant, this simplifies the morphology operators and the kernel matrix need not be stored explicitly at all, as was shown above.

Figure 5:
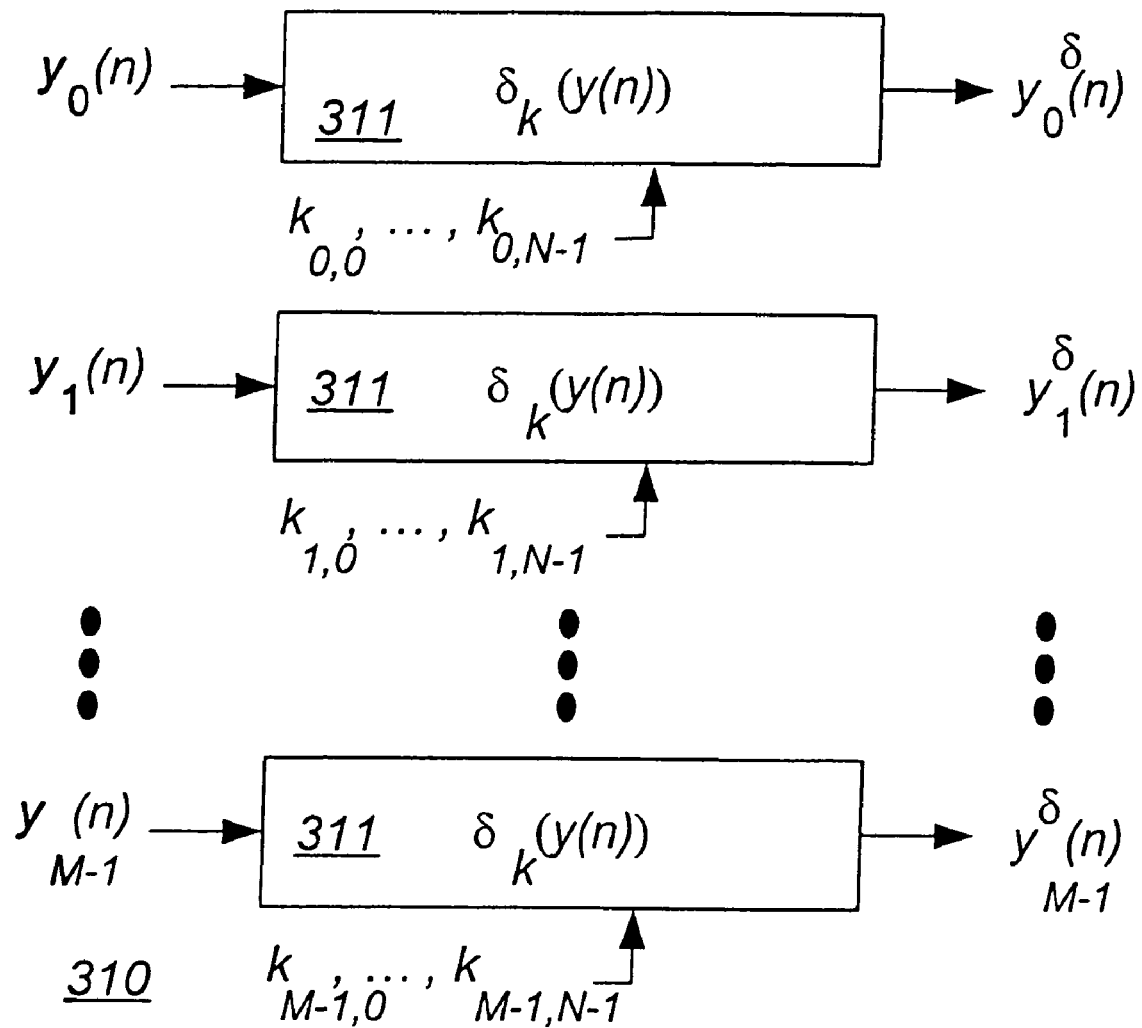
FIG. 5 is a functional block diagram of the multi-channel Dilate Filter Unit of the apparatus of FIG. 3.

FIG. 5 shows the internal multi-channel detail of Unit 310. The processing of each signal channel is an implementation of the Dilate mathematical morphology function defined above, where each row of the kernel matrix K is used by the corresponding signal channel.

Figure 6:
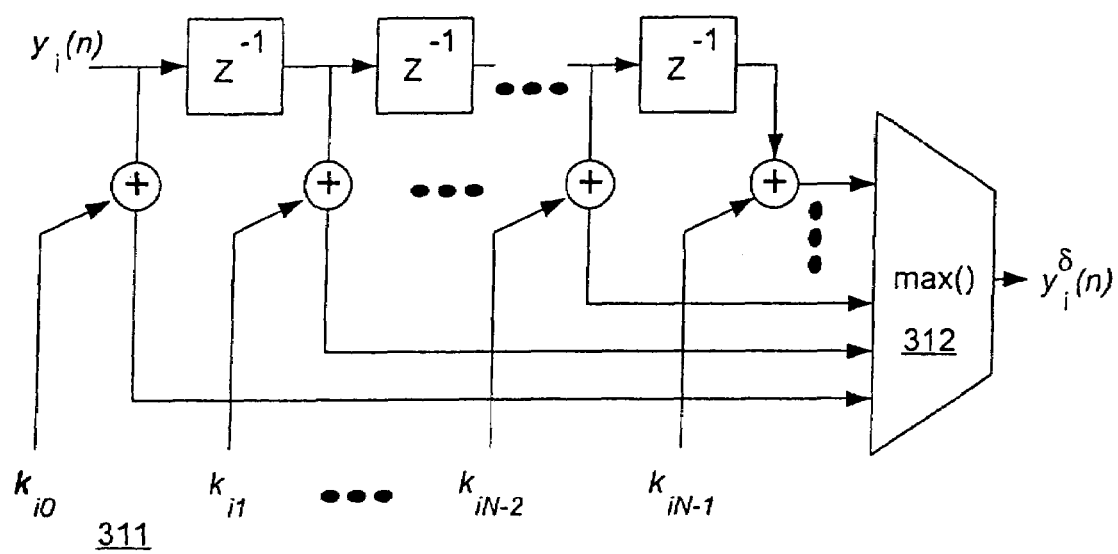
FIG. 6 is a functional block diagram of a Single-channel Dilate Filter of the apparatus of FIG. 3.

FIG. 6 shows the exact processing of Unit 311 to implement the Dilate function. Blocks with the symbol $z^{-1}$ define a one-sample time unit delay and their output values represent internal filter state. At each sample time, n, the max( ) operator 312 selects as its output the input with largest numerical value. It is well known how to translate these primitive operations into either a hardware or software implementation. For example, FIG. 7 illustrates a software implementation in the C programming language.

Figure 8:
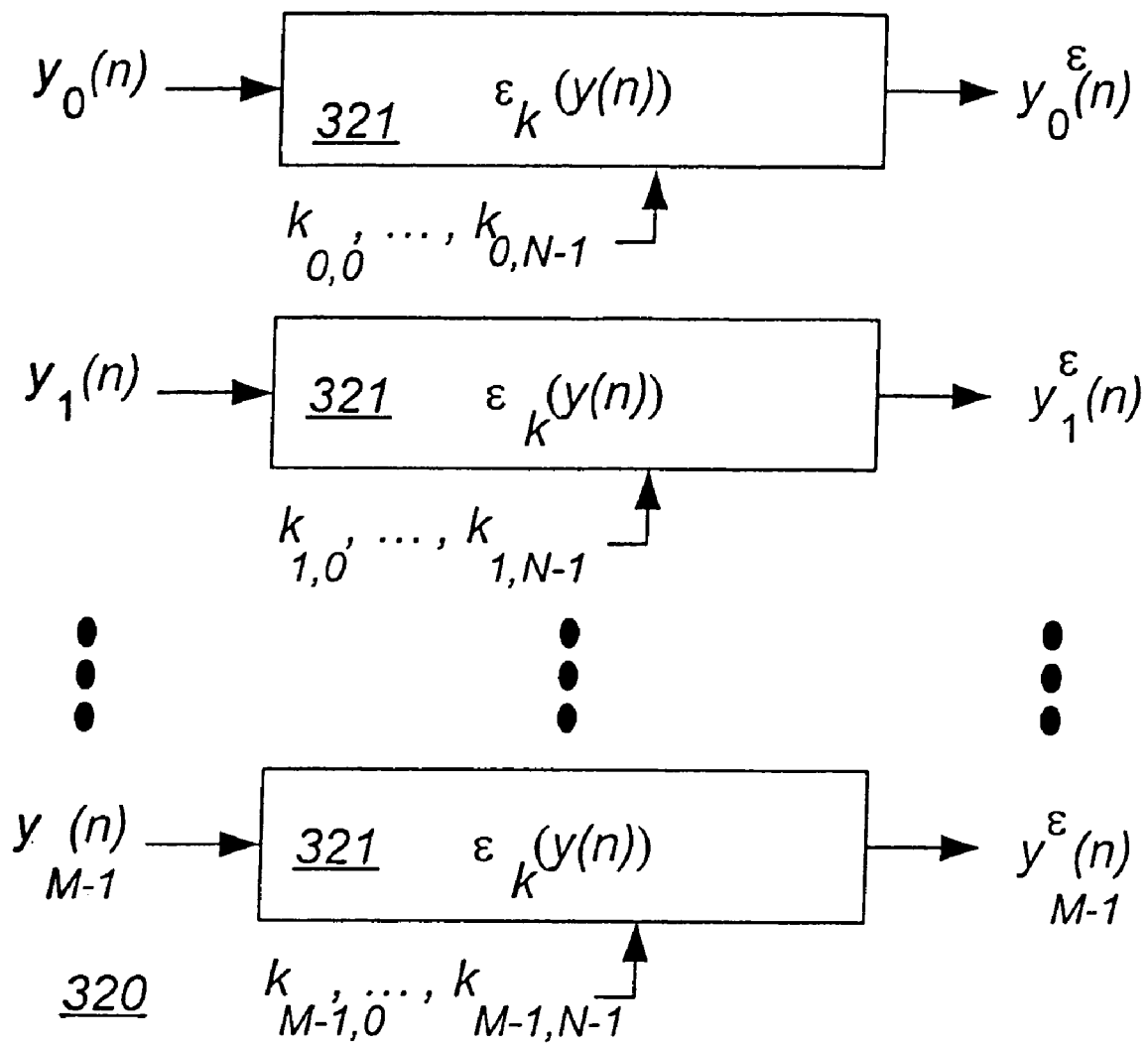
FIG. 8 is a functional block diagram of the multi-channel Erode Filter Unit of the apparatus of FIG. 3.

FIG. 8 shows the internal multi-channel detail of Unit 320. The processing of each signal channel is an implementation of the Erode mathematical morphology function defined above, where each row of the kernel matrix K is used by the corresponding signal channel.

Figure 9:
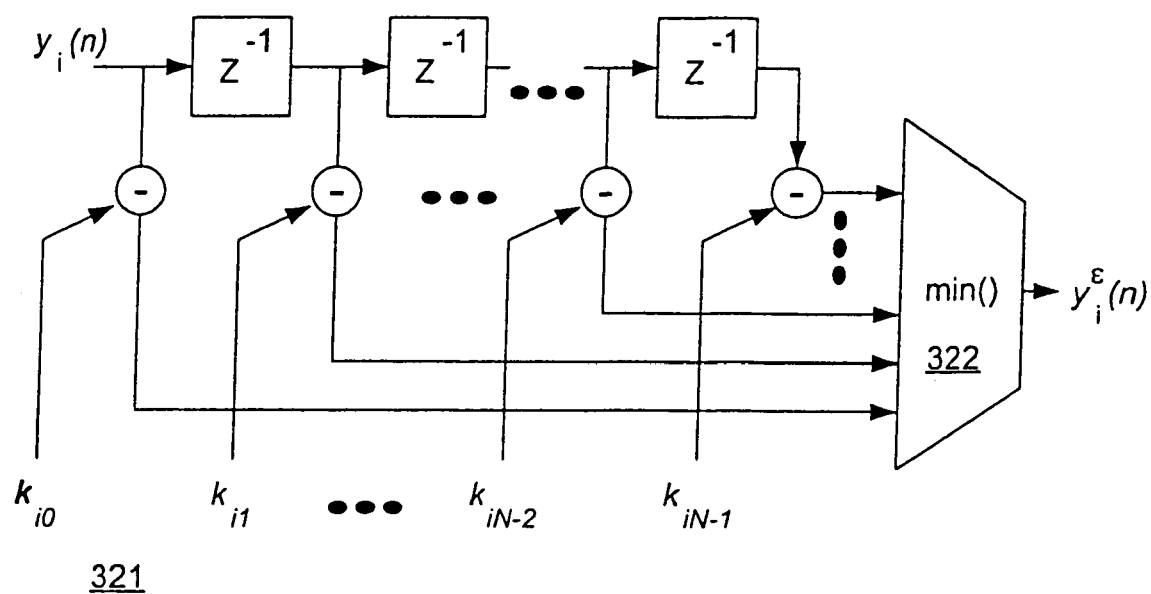
FIG. 9 is a functional block diagram of a Single-channel Erode Filter of the apparatus of FIG. 3.

FIG. 9 shows the exact processing of Unit 321 to implement the Erode function. At each sample time, n, the min( ) operator 322 selects as its output the input with the smallest numerical value. It is well known how to translate these primitive operations into either a hardware or software implementation. For example, such a software configuration is possible similar to that depicted for Unit 311 according to FIG. 7.

Figure 10:
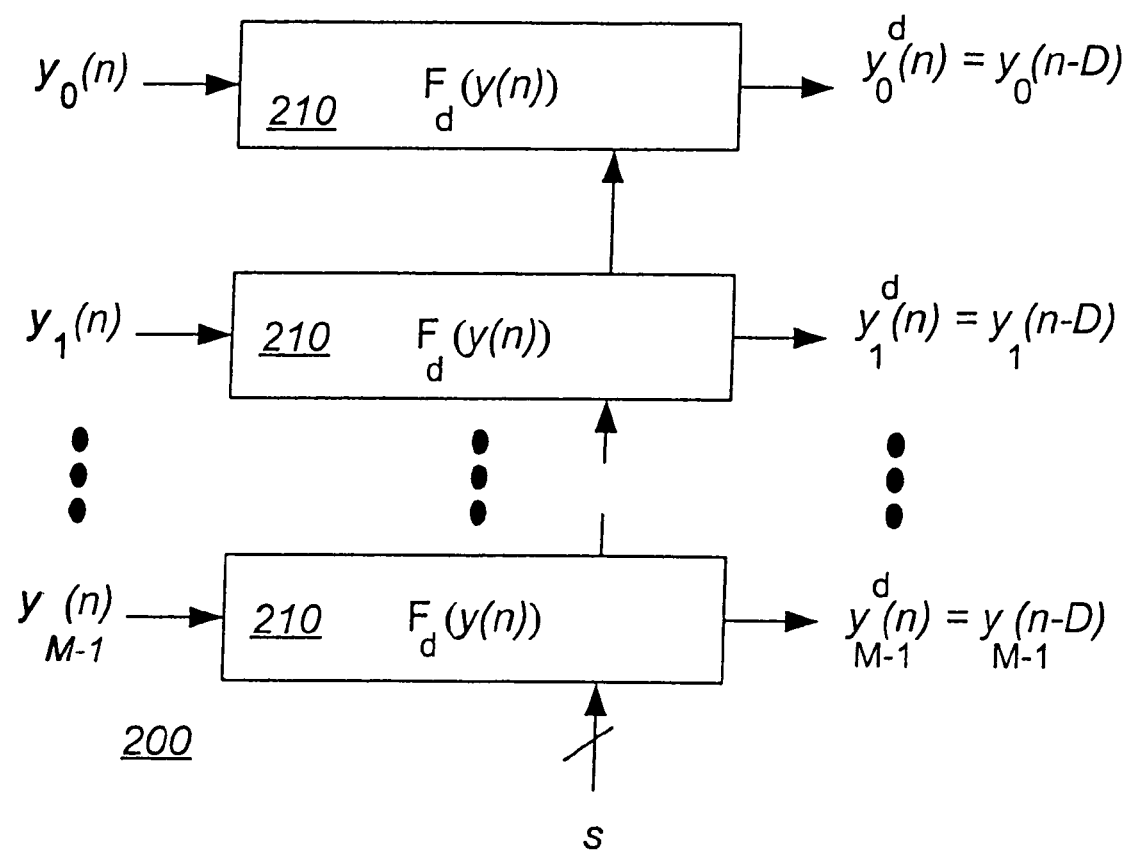
FIG. 10 is a functional block diagram of the multi-channel (selectable) Delay Filter Unit of the apparatus of FIG. 3.
Figure 11:
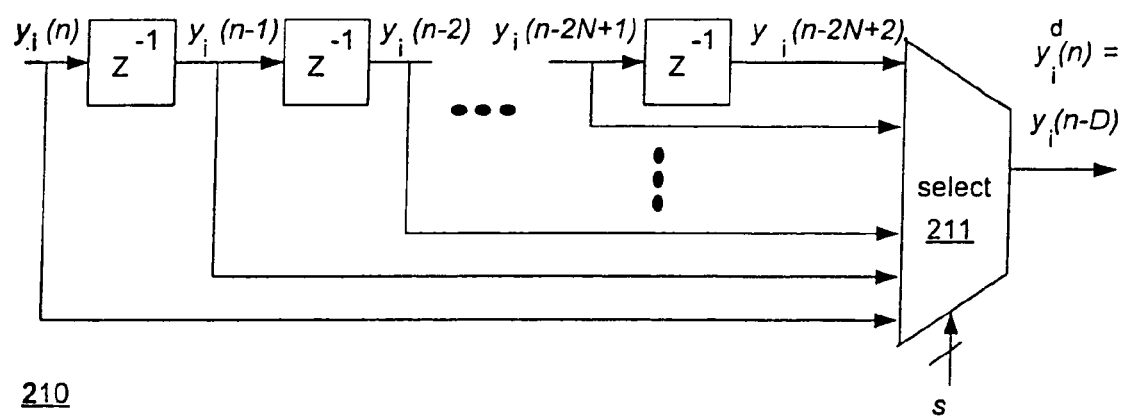
FIG. 11 is a functional block of the linear (selectable) Delay Filter Unit of the apparatus of FIG. 3.

A block diagram of linear Delay Operator 200 is shown in FIG. 10, and a detailed implementation diagram of each channel linear Delay Operator 210 is shown in FIG. 11. As in the preceding and in each diagram, the block $z^{-1}$ represents a constant one-sample delay and the total signal delay is selected in order to match the input/output signal delay of the Morphology Operator 300. Consider for example the kernel function:

$$k(n) = \begin{cases} c & \text{for } n = 0, 1, \ldots, N-1 \\ 0 & \text{otherwise} \end{cases}$$

A concatenation of the Dilate/Erode operators, $\delta_0(\epsilon_0(y(n)))$ or $\epsilon_0(\delta_0(y(n)))$, will cause a linear delay of N−1 samples for peaks and valleys that are wider than N samples. Hence, the concatenation $\delta_0(\epsilon_0(\epsilon_0(\delta_0(y(n)))))$ causes a linear delay of 2(N−1) for peaks and valleys that are wider than N samples. In this instance, the selection setting(s) for Delay Operator 200 would be 2(N−1). Other coefficient selections might imply an equal or lesser delay setting.

Figure 12:
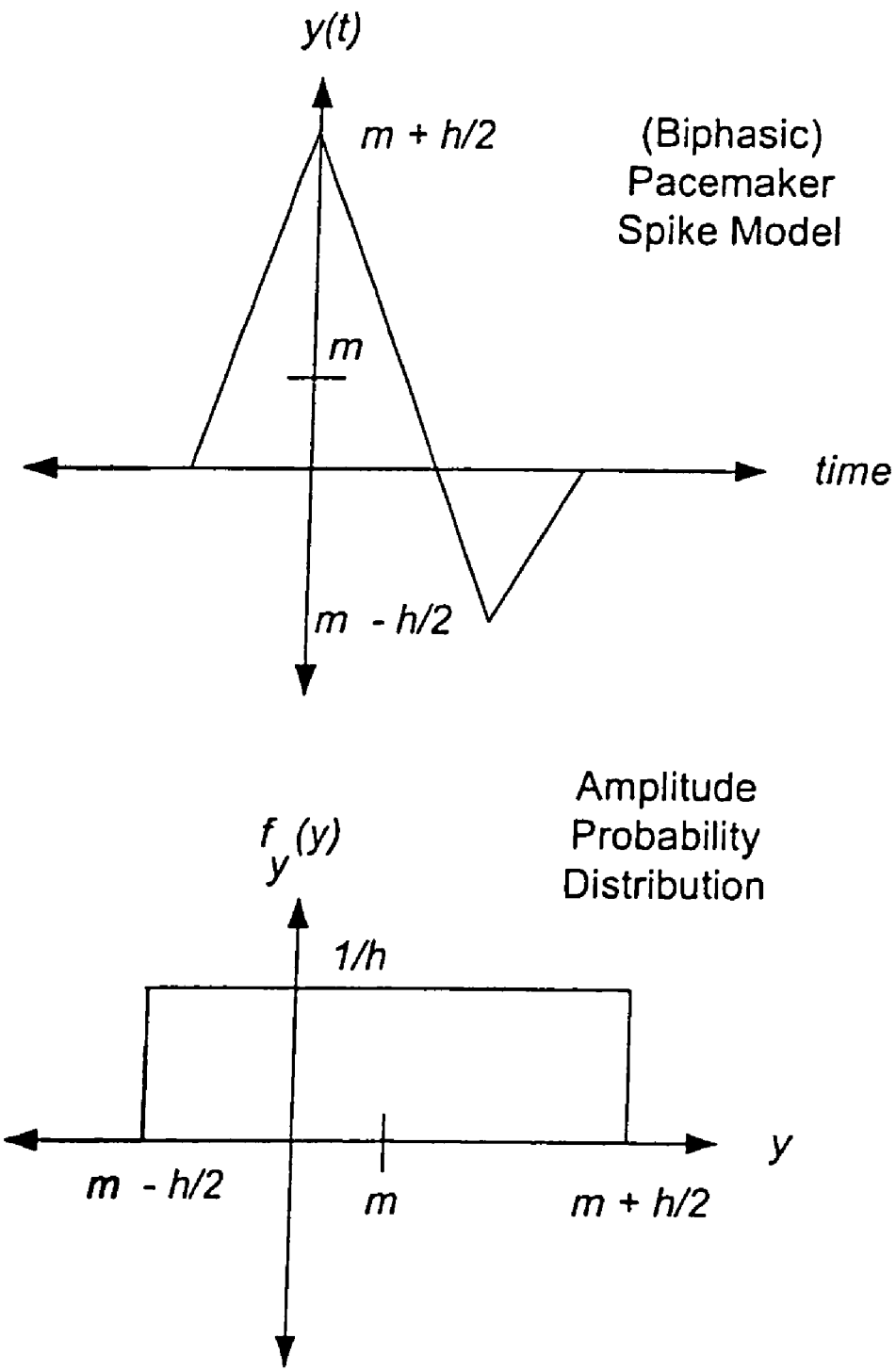
FIG. 12 depicts a pacer spike model and amplitude probability distribution.

If a (biphasic) pacer spike is modeled as a finite duration (ignoring overshoot and settling time) triangular pulse with a constant positive and negative slope as shown in FIG. 12, random samples of its amplitude values would be described by the uniform amplitude probability distribution, $f_y(y)$, also shown. This probability distribution is parameterized in terms of the spike mean, mi, and the maximum peak-to-peak variation in amplitude, h. The "average absolute deviation from the mean" $\xi(f_y)$ is given by, $$\xi(f_y) = \int |y - m| f_y(y) dy = \int_{m-h/2}^{m+h/2} \frac{|y-m|}{h} dy = h/4$$

Figure 13:
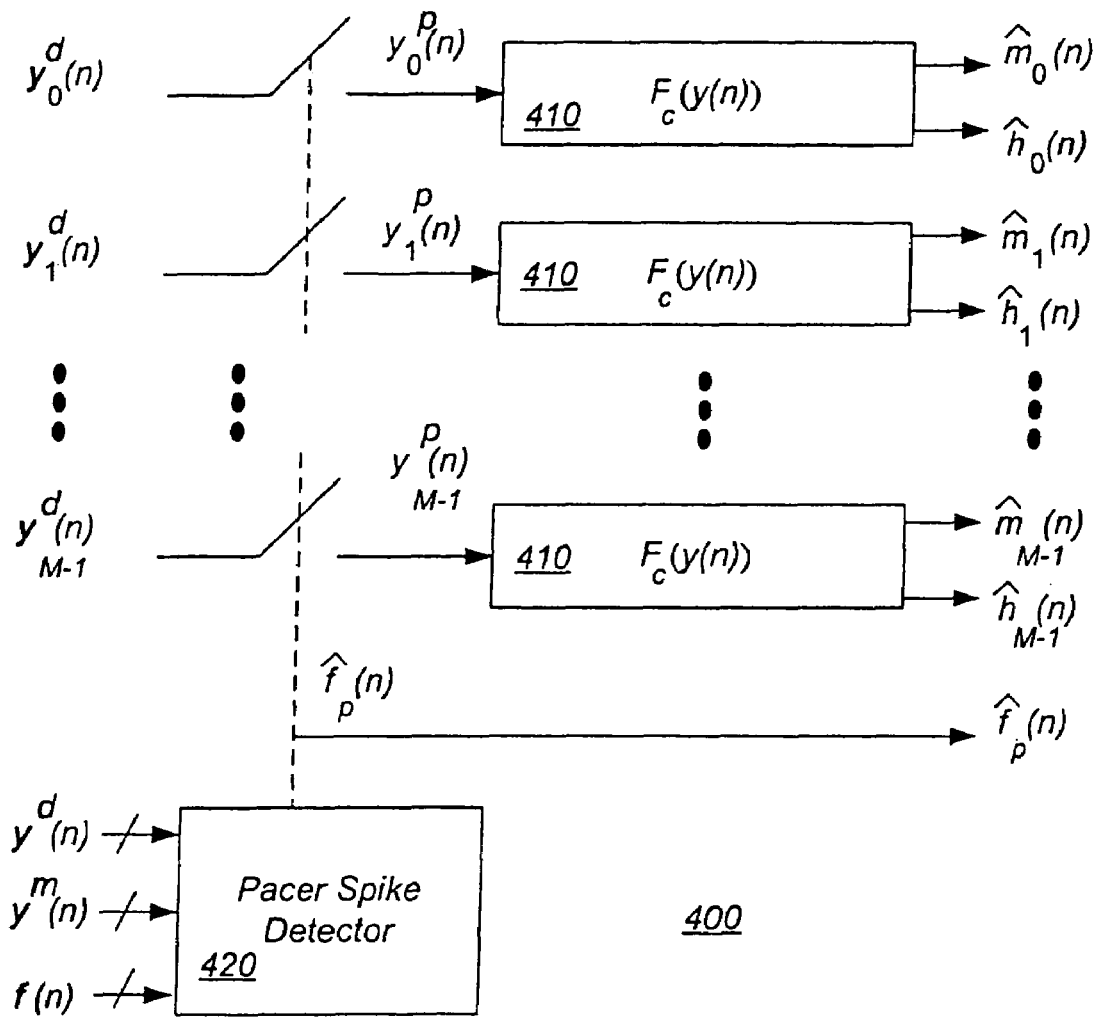
FIG. 13 is a functional block diagram of the multi-channel Pacer Spike Detector & Estimator Unit of the apparatus of FIG. 3.

FIG. 13 provides a detailed block diagram of the Pacer Spike Estimator 400 component of FIG. 3. Pacer Spike Estimator 400 calculates a mean estimate, $\hat{m}_i(n)$, and a maximum peak-to-peak variation estimate, $\hat{h}_i(n)$, of the main biphasic pacer spike using the accumulated history of spike sample values. Because sampling frequencies of the monitoring instrument are not synchronized with pacer firings, sample points along the pacer spike can be assumed to be random. The input to each estimator channel, $y_i^p(n)$, are those samples of the $y_i^d(n)$ that have pacer signal energy as determined by Pacer Spike Detector 420 shown in FIG. 15.

A mean estimate $\hat{m}(n)$ and average deviation estimate $\hat{\xi}(n)$ can be calculated directly from pacer spike samples, $y^P(0)$, $y^P(1), \ldots, y^P(n-1), \ldots$, using, $$\hat{m}(n+1) = F_1(y^P(n))$$

$$\hat{\xi}(n+1) = F_2(d(n)) \text{ where } d(n) = |y^P(n) - \hat{m}(n)|$$

$$\hat{m}(0) = 0 \text{ and } d(0) = 0 \text{ for } n < 0$$

where $$y^P(n) = \begin{bmatrix} y_0^P(n) \\ y_1^P(n) \\ \ldots \\ y_{M-1}^P(n) \end{bmatrix} \in \mathbb{R}^M, \quad \hat{m}(n) = \begin{bmatrix} \hat{m}_0(n) \\ \hat{m}_1(n) \\ \ldots \\ \hat{m}_{M-1}(n) \end{bmatrix} \in \mathbb{R}^M,$$

$$\hat{\xi}(n) = \begin{bmatrix} \hat{\xi}_0(n) \\ \hat{\xi}_1(n) \\ \ldots \\ \hat{\xi}_{M-1}(n) \end{bmatrix} \in \mathbb{R}^M$$

and in which $F_1(\bullet)$ and $F_2(\bullet)$ are multi-channel, finite-impulse response (FIR) or infinite impulse response (IIR) linear, low-pass filters. In general, the lower the cut-off frequency of these filters, the better is the performance, but the lower cut-off is burdened with additional computational overhead.

One simple, computationally efficient implementation uses a single-pole IIR for both $F_1(\bullet)$ and $F_2(\bullet)$, $$\hat{m}(n+1) = \alpha \hat{m}(n) + (1-\alpha) y^P(n)$$

$$\hat{\xi}(n+1) = \alpha \hat{\xi}(n) + (1-\alpha) |y_p(n) - \hat{m}(n)|$$

where $0 < \alpha < 1$

The constant $\alpha$ is a tunable parameter that is used to weight the new data relative to the last estimate. Generally $\alpha$ will have a value close to 1 (e.g. about 0.8 or 0.9), but must have a value less than 1 for the estimator to be stable. It can be tuned for optimal performance using input pacer spikes with known characteristics.

Combining the deviation estimate with the above amplitude probability distribution mean deviation formula, a running estimate of the peak-to-peak amplitude variation, $\hat{h}(n)$ is, $$\hat{\xi}(n) = \hat{h}(n)/4 \Rightarrow \hat{h}(n) = 4\hat{\xi}(n)$$

Figure 14:
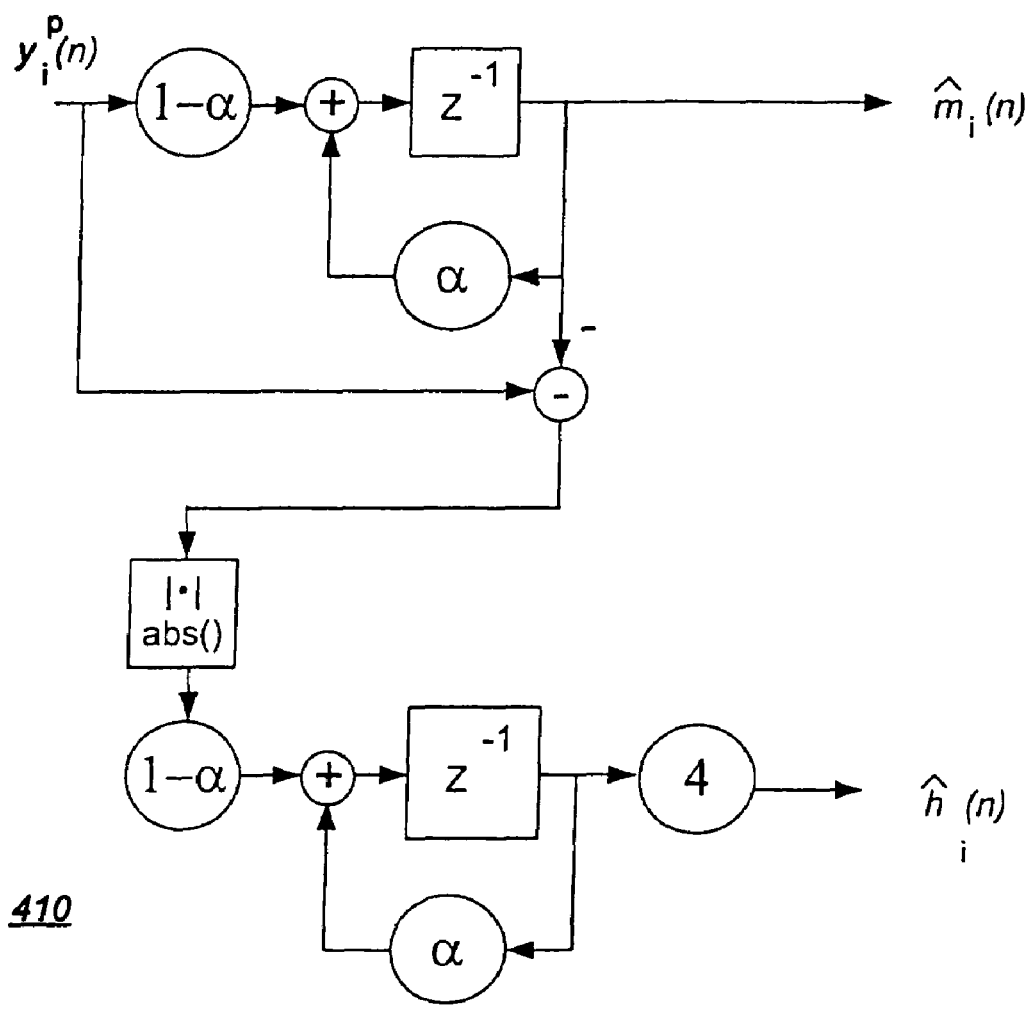
FIG. 14 is a functional block diagram of a single channel Pacer Spike Estimator of the apparatus of FIG. 3.

These computations are implemented by each channel estimator $F_c(\bullet)$ 410 in FIG. 13. FIG. 14 shows the explicit implementation of each estimator 410, where it is well known how to translate these primitive operations into either a hardware or software implementation.

There are many other possibilities and variations for the estimator that would also be suitable. For example, another measure for the "deviation from the mean" is the variance $$\sigma^2(f_y) = \int (y-m)^2 f_y(y) dy = \int_{m-h/2}^{m+h/2} \frac{(y-m)^2}{h} dy = h^2/12$$

which can be recursively estimated from the pacer signal samples using $$\hat{\sigma}^2(n+1) = \alpha \hat{\sigma}^2(n) + (1-\alpha)(y^P(n) - \hat{m}(n))^2$$

In this case, a running estimate of the peak-to-peak amplitude variation, $\hat{h}(n)$ is, $$\hat{\sigma}^2(n) = \hat{h}(n)^2/12 \Rightarrow \hat{h}(n) = \sqrt{12\hat{\sigma}^2(n)} = 2\sqrt{3\hat{\sigma}^2(n)}$$

Compared to the "mean deviation" based estimator above, this estimator requires additional multiplications and a square-root calculation.

Figure 15:
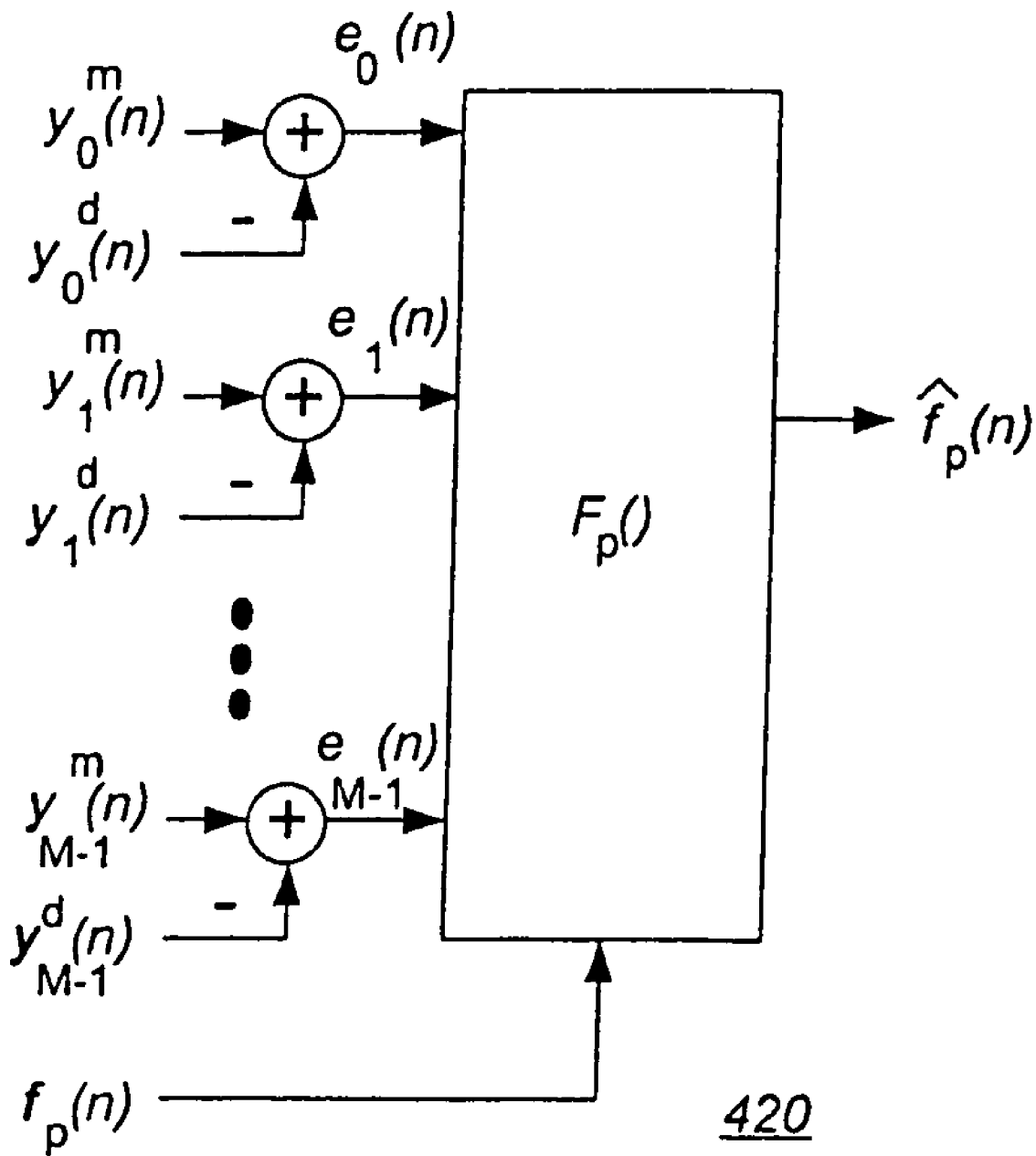
FIG. 15 is a functional block diagram of the Pacer Spike Detector of the apparatus of FIG. 3.

FIG. 15 shows a block diagram of Pacer Spike Detector 420. Operator $F_p(\ )$ has as inputs the difference between all channels of Delay Operator 200 and the Morphology Operator 300. Because the latter strips the pacer signal, a large difference would indicate the presence of a pacer spike. All channels are used to provide the most amount of information to the detector, which, for example, increases robustness to false detection due to noise spikes that occur on only one channel. An external pacer flag signal $f_p(n)$ is an additional optional input to provide the final detection decision.

Operator $F_p(\ )$ could take any number of forms. For example, $$\hat{f}_p(n) = \begin{cases} 1 & \text{if } e^T W e \geq \beta \text{ or } f_p(n) = 1 \\ 0 & \text{otherwise} \end{cases}$$

where $$W = \begin{bmatrix} w_{00} & w_{01} & \cdots & w_{0M-1} \\ w_{10} & w_{11} & 0 & \vdots \\ \vdots & 0 & \ddots & 0 \\ w_{1M-1} & \cdots & 0 & w_{M-1M-1} \end{bmatrix}, \quad e(n) = \begin{bmatrix} e_0(n) \\ e_1(n) \\ \ldots \\ e_{M-1}(n) \end{bmatrix} \in \mathbb{R}^M$$

and $e_i(n) = y_i^m(n) - y_i^d(n)$ is the difference between ECG channel i of the linear delay filter 200 and the same channel of morphology filter 300. The weight values are used to relatively compare $e_i(n)$ from each signal channel. Specific characteristics of the environment, such as the channel signal-to-noise ratio, determine the value of the weights. Generally, the weights will be positive, but need not be, and generally matrix W will be positive-definite, i.e. $x^T W x > 0$ for all non-zero vectors x. If the weighted sum of magnitude-squared error is greater than threshold $\beta$, or the external signal flags a pacer, then this detector also flags a pacer. In this case the external signal is assumed to be significantly more reliable, and so overrides internal detection. In practice, many of the weight values may be equal to 0, in which case they neither need to be stored nor explicitly used in computation.

Another possible form for operator $F_p(\ )$ is:

$$\hat{f}_p(n) = \begin{cases} 1 & \text{if } [e^T f_p(n)] W \begin{bmatrix} e \\ f_p(n) \end{bmatrix} \geq \beta \\ 0 & \text{otherwise} \end{cases}$$

where $$W = \begin{bmatrix} w_{00} & w_{01} & \cdots & w_{0M} \\ w_{10} & w_{11} & 0 & \vdots \\ \vdots & 0 & \ddots & 0 \\ w_{1M-1} & \cdots & 0 & w_{MM} \end{bmatrix}, \quad e(n) = \begin{bmatrix} e_0(n) \\ e_1(n) \\ \ldots \\ e_{M-1}(n) \end{bmatrix} \in \mathbb{R}^M$$

In this case, the external signal is relatively weighted against the difference signal $e_i(n)$ each channel. It is also possible to select the weights of this form so that the results are the same as the previous $F_p(\ )$, but the computational burden would typically be greater.

Figure 16:
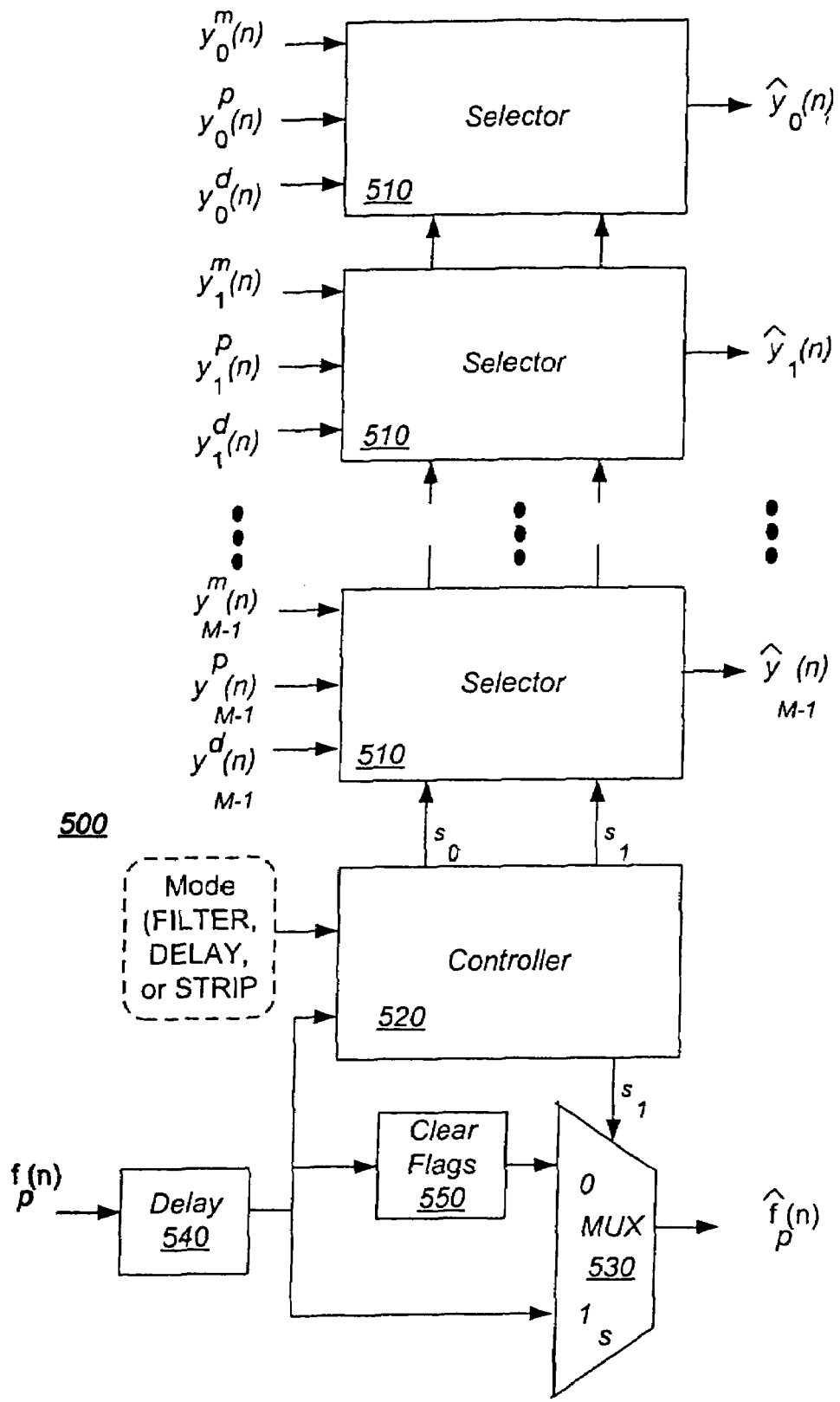
FIG. 16 is a functional block diagram of the multi-channel Coordinator Unit of the apparatus of FIG. 3.
Figure 17:
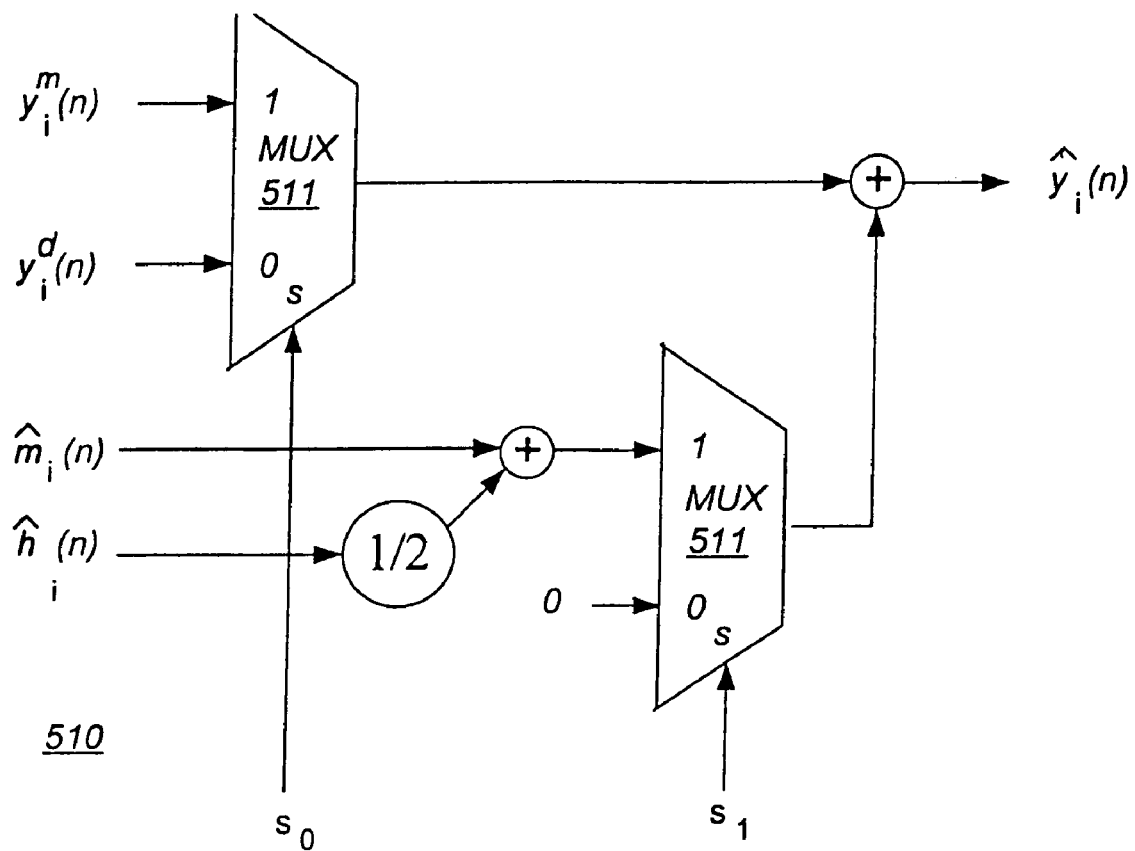
FIG. 17 is an implementation diagram of a single channel of the Coordinator Unit of FIG. 16.

A block diagram of the Coordinator 500 is shown in FIG. 16. Controller 520 uses the output of the Delay Operator 200 or the Morphology Operator 300 to dynamically select the final output of each channel. Because these filters operate on the input data stream in parallel, and there is no feedback of the output back into either filter, dynamically switching between the two outputs creates no transient response effects. FIG. 17 shows the detailed implementation of each Selector 510. A multiplexor (MUX) 511 selects the 0 input if selector input s=0 or the 1 input for s=1.

Figure 18:
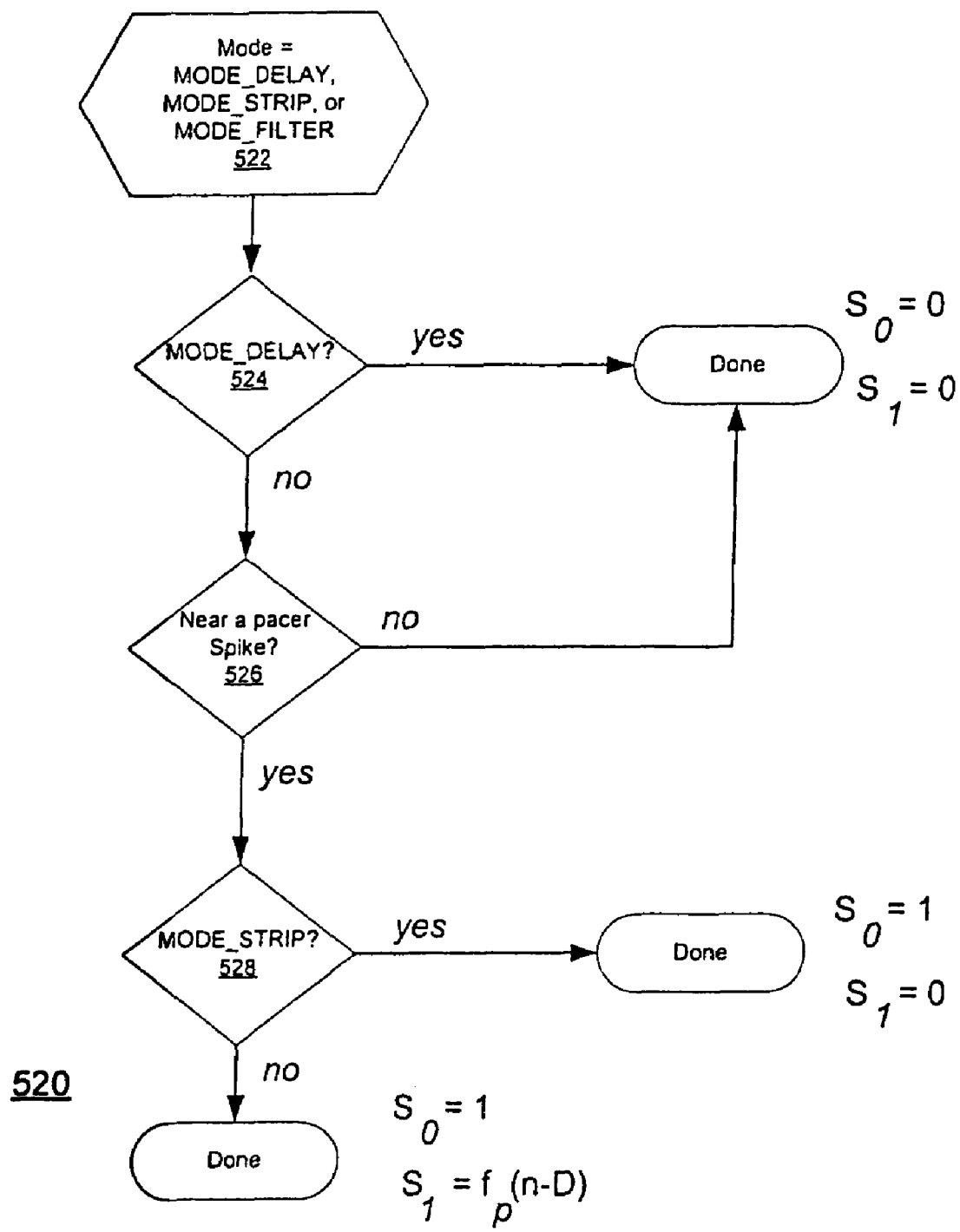
FIG. 18 is a flow chart describing the control function of the Coordinator Unit of FIG. 16.

FIG. 18 shows a flow chart of the exact control function executed by Controller 520. Note that one of the inputs to this controller 520 is a pacer "marker" or "flag" signal $f_p(n)$, indicating the presence of a pacer spike.

A reliable and simple method and apparatus has been disclosed for detecting, removing, or improving fidelity of the pacer signal in the ECG at low sampling rates. The method involves morphological operators that do not require any digital multiplications or significant digital storage. This means that the herein described method can be readily and inexpensively implemented in small instruments using either hardware or software as shown in the above description and associated figures. The method also works for normal or malfunctioning pacers that file at any phase relative to the QRS complex in the ECG signal. The method may also be used to estimate the height and polarity of the pacer signal spike, even though the sampling time period may be longer than the maximum period specified by the well-known Nyquist limit for reconstructing a band-limited continuous signal from its samples. In fact, the sampling period can be longer than the time width of the spike itself.

It will be readily apparent that there are other modifications and variations which can be employed by those of sufficient skill employing the intended scope of the invention according to the following claims.

What is claimed is:

1. A method to at least one of detecting, removing and estimating a pacemaker pacer signal from an electrocardiogram ("ECG") signal of a human or animal to diagnose a physiological condition, said method comprising the steps of:
   digitizing a plurality of ECG potentials (M channels of ECG lead data) with an analog to digital converter ("ADC") to create a discrete signal representation of each potential in time;
   filtering the plurality of ECG potentials using a digital filter to create a plurality of filtered ECG potentials;
   operating on the plurality of filtered ECG potentials using a non-linear mathematical morphology function to detect and remove the pacer maker signal from the ECG signal to create a plurality of processed ECG potentials wherein the step of operating on the plurality of filtered ECG potentials using a non-linear mathematical morphology function further comprises the step of estimating the pacer signal height using sampling rates that may be below the Nyquist rate; and
   diagnosing a physiological condition of the human or animal based on the processed ECG potentials.

2. The method of claim 1 wherein the step of operating on the plurality of filtered ECG potentials using a non-linear mathematical morphology function comprises the additional step of using a dilate mathematical morphology function.

3. The method of claim 1 wherein the step of operating on the plurality of filtered ECG potentials using a non-linear mathematical morphology function comprises the additional step of using an erode mathematical morphology function.

4. The method of claim 1 wherein the step of operating on the plurality of filtered ECG potentials using non-linear mathematical morphology functions comprises the additional step of using both a dilate and an erode mathematical morphology function.

5. The method of claim 4 wherein the step of operating on the plurality of filtered ECG potentials using the non-linear dilate and erode mathematical morphology functions removes ECG signal peaks and valleys caused by the pacer signal creating a clean QRS complex waveform free of significant distortion caused by the pacer signal.

6. The method of claim 5 wherein operating on the plurality of filtered ECG potentials using the non-linear dilate and erode mathematical morphology functions removes ECG signal peaks and valleys having widths smaller than a specified threshold while preserving the integrity of peaks and valleys wider than the specified threshold associated with a QRS complex in the ECG potential.

7. The method of claim 6 wherein operating on the plurality of filtered ECG potentials using a non-linear mathematical morphology function to detect and remove the pacer signal from the ECG signal to create a plurality of processed ECG potentials comprises detecting and removing a pacer signal from the ECG signal that has lost proper phasing or synchronization with the QRS complex.

8. The method of claim 1 wherein the step of diagnosing a physiological condition of the human or animal based on the processed ECG potentials further comprises the additional step of detecting and diagnosing a pacemaker failure condition based on the detected pacer signal.

9. The method of claim 8 wherein the step of detecting and diagnosing a pacemaker failure condition comprises the additional step of detecting and diagnosing loss of pacemaker phase reference to the QRS complex or loss of pacemaker synchronization with the QRS complex.

10. The method of claim 1 further comprising the step of comparing the plurality of filtered ECG potentials to the plurality of processed ECG potentials by delaying the filtered ECG potentials in order to match a signal delay caused by the mathematical morphology function.

11. The method of claim 1 wherein digitizing a plurality of ECG potentials (M channels of ECG lead data) with an analog to digital converter ("ADC") to create a discrete signal representation of each potential in time further comprises the step of detecting a pacer signal using an analog pacer detector to associate a flag with nearest points in the discrete signal representation of the ECG potentials.

12. The method of claim 11 wherein detecting pacer signals using an analog pacer detector comprises detecting a pacer signal that coincidentally falls between two points in the discrete signal created by the ADC such that at least one instance of a sub-Nyquist pacer signal would otherwise go undetected by the ADC.

13. An electrocardiogram ("ECG") apparatus to at least one of detecting, removing and estimating pacemaker pacer signals from an ECG waveform to diagnose a physiological condition of a human or animal, said apparatus comprising:
   ECG electrodes to pickup a plurality of ECG potentials (M channels of ECG lead data) from the body of the human or animal being diagnosed, the electrodes electrically coupled to the body and connected to an ECG input;
   an analog to digital converter ("ADC") electrically connected to the ECG input, the ADC to digitize the ECG potentials and to create a discrete signal representation of each potential in time;

a filter block electrically coupled to the ADC to transfer the discrete signal representation of each potential in time to the filter block, the filter block to perform digital filtering on the discrete signal representation of each potential and to create a plurality of filtered ECG potentials;

a non-linear pacer filter electrically coupled to the filter block to receive the plurality of filtered ECG potentials, the non-linear pacer filter to perform at least one non-linear mathematical morphology function on the filtered ECG potentials to detect and remove the pacer signal from the ECG waveform and to create at least one processed ECG waveform; and a display to allow viewing of the processed ECG waveform to diagnose a physiological condition of a human or animal based at least in part on the viewing of the processed ECG waveform wherein the non-linear pacer filter further comprises:

- a delay operator to shift the at least one processed ECG waveform in time so that the signal can be compared to signals and events unmodified by the morphology operator;
- a morphology operator to perform a series of concatenated dilate/erode mathematical morphology functions on the plurality of filtered ECG potentials; and
- a pacer spike detector/estimator to calculate a mean estimate and a peak to peak variation estimate of a main biphasic pacer spike using an accumulated history of spike sample values.

14. The apparatus of claim 13 wherein the non-linear pacer filter performs at least one non-linear erode mathematical morphology function.

15. The apparatus of claim 13 wherein the non-linear pacer filter performs at least one non-linear dilate mathematical morphology function.

16. The apparatus of claim 13 wherein the non-linear pacer filter performs cascaded non-linear erode and dilate mathematical morphology functions.

17. The apparatus of claim 13 wherein the delay operator causes a linear delay suitable to the number and type of concatenated dilate/erode operators performed by the morphology operator.

18. The apparatus of claim 13 wherein the pacer spike detector/estimator comprises at least one FIR or at least one IIR digital filter to perform low pass filtering as part of the mean estimate and an average deviation calculation.

19. The apparatus of claim 13 wherein a deviation from the mean calculation performed in the pacer spike detector/estimator is a variance, the variance recursively estimated from a plurality of pacer signal samples.

20. The apparatus of claim 13 wherein differences between a time shifted signal from the delay operator and a processed signal from the morphology operator are used to indicate the presence of a pacer spike.

21. The apparatus of claim 20 further comprising an analog pacer detector to detect a sub Nyquist pacer signal wherein the pacer signal falls between two points in the discrete signal created by the ADC such that at least one instance of the pacer signal would otherwise go undetected by the ADC.

22. The apparatus of claim 21 wherein analog detection of a pacer signal causes a flag or marker that can be delayed by a delay operator to match in time a signal processed and delayed by a morphology operator.

23. The apparatus of claim 13 wherein a marker or a flag signal indicates the presence of a pacer spike.

24. The apparatus of claim 13 wherein the non-linear mathematical morphology function is carried out in software or in hardware.

* * * * *